United States Patent [19]

Székely et al.

[11] Patent Number: 4,671,871
[45] Date of Patent: Jun. 9, 1987

[54] CHROMATOGRAPHIC SHEET AND/OR A SYSTEM OF CHROMATOGRAPHIC SHEETS FOR OVERPRESSURED MULTILAYER CHROMATOGRAPHY

[75] Inventors: Tibor Székely; Ernö Tyihák, both of Budapest; Emil Mincsovics, Szentendre; Zsuzsa Remenyi nee Korodi, Budapest; Laszlo Peterfi, Budapest; Gabor Kemeny, Budapest; Gabor Takacs, Budapest, all of Hungary

[73] Assignee: Labor Muszeripari Muvek, Budapest, Hungary

[21] Appl. No.: 898,847

[22] Filed: Aug. 19, 1986

Related U.S. Application Data

[63] Continuation of Ser. No. 668,302, Nov. 5, 1984, abandoned.

[51] Int. Cl.$^4$ .............................................. B01D 15/08
[52] U.S. Cl. ............................. 210/198.3; 210/502.1; 210/658
[58] Field of Search ............... 210/656, 657, 658, 659, 210/198.2, 198.3, 502.1

[56] References Cited

U.S. PATENT DOCUMENTS

| | | | |
|---|---|---|---|
| 2,986,280 | 5/1961 | Magnuson | 210/657 |
| 3,503,712 | 3/1970 | Sussman | 210/198.2 |
| 3,864,263 | 2/1975 | Jethwa | 210/198.3 |
| 4,139,458 | 2/1979 | Harrison | 210/657 |
| 4,272,381 | 6/1981 | Kremer | 210/198.3 |
| 4,346,001 | 8/1982 | Tyihak | 210/198.3 |
| 4,469,601 | 9/1984 | Beaver | 210/198.3 |

OTHER PUBLICATIONS

"Optimization of Operating Parameters in Overpressured Thin-Layer Chromatography", E. Tyihak, E. Mincsovics, H. Halasz and J. Nagy, Journal of Chromatography, 211 (1981), pp. 45–51.
"Applicability of OPTLC in Analysis of Various Substance Groups", E. Tyihak, T. J Szekely and E. Mincsovics; publication, Instrumental High Performance Thin Layer Chromatography, Interlaken (1982), 13, pp. 159–172.

Primary Examiner—Ernest G. Therkorn
Attorney, Agent, or Firm—Mandeville and Schweitzer

[57] ABSTRACT

The present invention relates to a chromatographic sheet and/or a system of chromatographic sheets for overpressured multilayer chromatography.

One or more chromatographic sheets with sorbent layer are optionally sealed at their edges preferably by impregnation or coating with a polymer film and holed at the solvent inlet in adequate size and shape and they are optionally included in a system in single or multiple layers with or without a conventional chromatographic sheet sealed at its edges.

13 Claims, 16 Drawing Figures

CHROMATOGRAPHIC SHEET AND/OR A SYSTEM OF CHROMATOGRAPHIC SHEETS FOR OVERPRESSURED MULTILAYER CHROMATOGRAPHY

This is a continuation of application Ser. No. 668,302, filed Nov. 5, 1984, now abandoned.

BACKGROUND OF THE INVENTION

The present invention relates to a special chromatographic sheet and a system of chromatographic sheets. The chromatographic sheet or the system of chromatographic sheets of the invention enables the user to develop several chromatograms simultaneously by over-pressured layer chromatographic technique.

Late years the liquid chromatography techniques of planar as well as coloumn arrangement have undergone a speedy development. The coloumn-arranged, high-performance liquid chromatography (HPLC) (see J. J. Kirkland /ed./: Modern Practice of Liquid Chromatography, Wiley, N.Y., 1971) and the so-called high-performance thin-layer chromatography (HPTLC) (see W. Bertsch, S. Hara, R. E. Kaiser and A. Zlatkis: Instrumental HPTLC, Huthig, Heidelberg, 1980) were developed. The most important features of this latter one are the use of adsorbents comprising fine particles and a high degree of instrumentation. The fact, that effective separation can be achieved only on fine-particle sorbent layers indicates the restricted applicability of the technique of HPTLC, as good resolution is provided only in shorter distances. It was reasonable to develop a technique which is on the one hand similar to the coloumn chromatographic technique from the point of view of the well-standardizable conditions, on the other hand possesses with the essential advantages of the thin-layer chromatographic (TLC) technique (the possibility of visual evaluation, the possibility for using aggressive agents, the maplike identification).

These requirements are satisfied by a technique what is called overpressured layer chromatography (OPLC) which unifies the advantages of HPLC, HPTLC and the classical TLC. The essential apparatus of this technique is the pressurized ultramicro chamber in which the sorbent layer (e.g. silica gel, talcum, etc.) is completely covered preferably with a flexible membrane and this membrane is pressed in a cushion-like manner against the sorbent layer, thus the vapour space over the layer is eliminated. The micropump charging the eluent passes the eluent into the sorbent layer with an adjustable forced flow (see Hungarian Patent specification No. 173,749; British patent specification No. 1,570,760). There is possibility for linear development in one or two directions, as well as circular and triangular (anticircular) development by changing the place and shape of the eluent inlet.

The main advantage of OPLC are over TLC and the modern HPTLC:
 the development can be carried out in a shorter time,
 due to the quicker development the diffusion is less, the spots and bands are smaller, the number of theoretical plates increases,
 the development can be carried out even by viscous eluent mixtures or which badly wet the sorbent layer, and which chromatogram could not or could hardly be developed by conventional means.

In order to achieve a linear chromatogram by the aid of OPLC where the components are effectively separated, the edges of sorbent layers being on the chromatographic sheets must be suitably sealed by removing the sorbent from the edges of the layer, closing them with a sealent and covering them with an elastic foil. Thus the eluent cannot escape due to overpressure. But that is not enough for providing an effective separation. The travelling of the eluent with a linear front can be assured by the formation of a channel adjoining the eluent inlet.

This problem is solved by a flexible, replacable sheet (plate) protecting the cushion, too which is superposed to the sorbent layer. On the sheet (gap block) one or several channels are formed next to the eluent inlet on the side connecting to the sorbent layer.

By this time in the apparatuses of the over-pressured layer chromatographic techniques only one chromatographic sheet could be developed, though the efficiency of this techniques could be significantly increased if more than one chromatographic sheet were able to be developed simultaneously. The technique of OPLC as the classical technique of TLC gives a preferable possibility to use different specific colour reactions, but when a large number of samples has to be compared, each chromatographic sheet has to be developed separately, which takes a long time and a great place. The OPLC also needs the use of chromatographic sheets with different sorbent layers, but in order to choose the suitable eluent a great number of experiments has to be carried out.

SUMMARY OF THE INVENTION

In working out the invention, the aim was to develop a chromatographic sheet (chromatoplate) or a system of the said sheets which meet these requirements.

The invention is based on the recognition that an apparatus of the overpressured layer chromatography is suitable for the development of several chromatographic sheets simultaneously if the said chromatographic sheets are specially modified in order to satisfy the said requirements, i.e. they are holed in a suitable shape and size adjoining the eluent inlet.

If the hole were made in the middle of the chromatographic sheets, after superposing onto one on another these sheets are suitable for circular multilayer development. This is very preferable for the quick screening of a large number of samples.

Furthermore, the invention is based on the recognition that the simultaneous linear development of the chromatograms can be achieved on several chromatographic sheets if the said chromatographic sheets holed in suitable size and shape, sealed on their edges are thus included in a system consisting of the said sheets and one conventional sheet sealed at its edges but unholed that this latter one is used as the lowest member.

The system of chromatographic sheets can also be created by using the former holed sheets only, but then a polymer foil, e.g. polyethylene or tephlon foil has to be put under the lower sheet as closure member.

The spreading of the eluent on the different chromatographic sheets which is a condition of the linear development can be solved in different manners:
 one or several channels leading the eluent can be cut into the sorbent layer,
 one or several channels or edges leading the eluent can be made on the sheet working in a cushion-like manner, the perforation is made at right angles to the direction of the migration of the eluent and its shape is a longitudinal slit, each sorbent layer can be covered by a perforated sheet supplied with leading channel or edge.

Furthermore, the invention is based on the recognition that chromatographic sheets with different kinds of sorbent layers can be employed in said sheet system, thus an eluent can be tested on several sorbent layers simultaneously.

Furthermore, the invention is based on the recognition that if the same samples are tested simultaneously then after the development there is possibility to apply different reagents and their quantitative comparison can be made.

DESCRIPTION OF THE INVENTION

Figure 1:
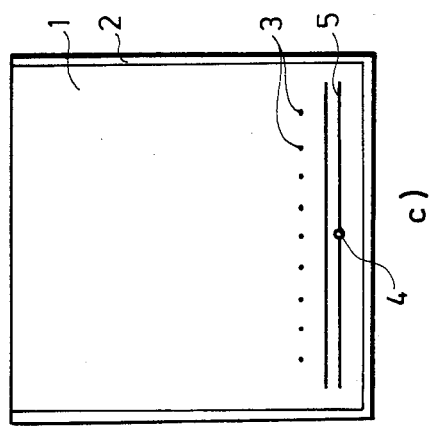
FIG. 1 is a plan view of chromatographic sheets used for one-directional development in the overpressured chromatographic system of the invention.
Figure 1:
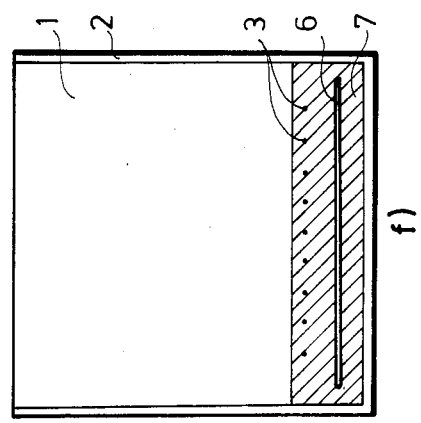
Figure 1:
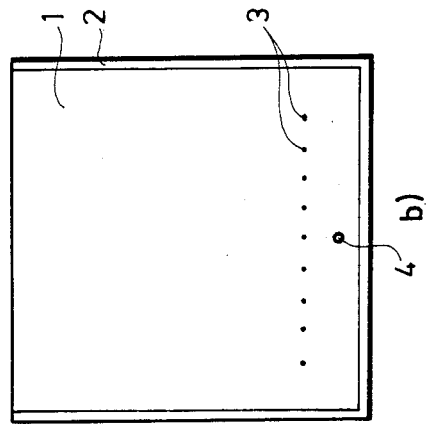
Figure 1:
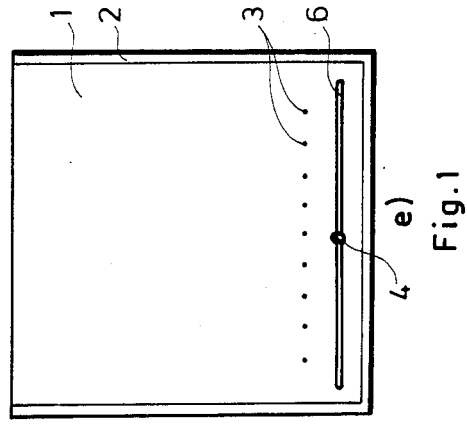
Figure 1:
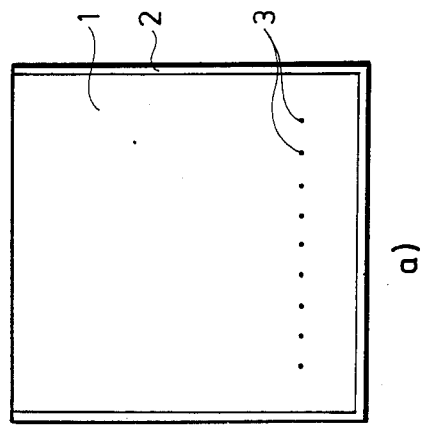
Figure 1:
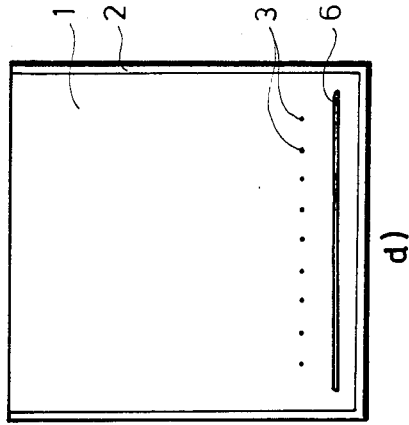
Figure 2:
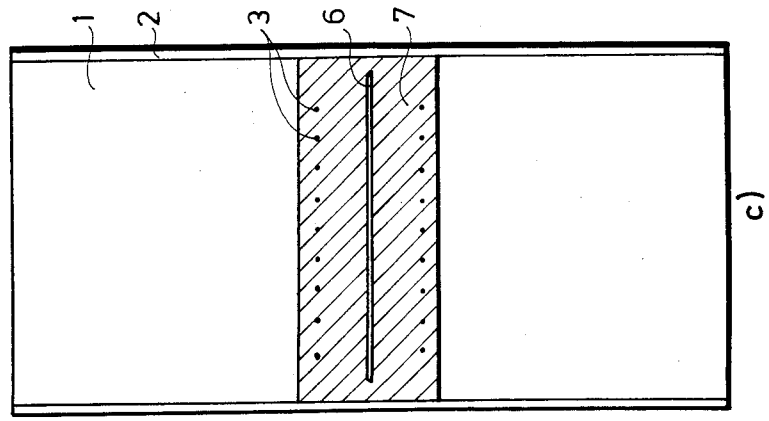
FIG. 2 is a plan view of chromatographic sheets used for two-directional development in the overpressured chromatographic system of the invention.
Figure 2:
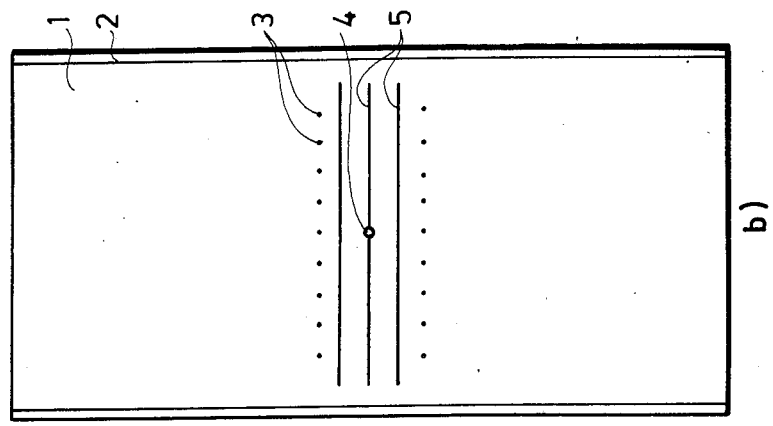
Figure 2:
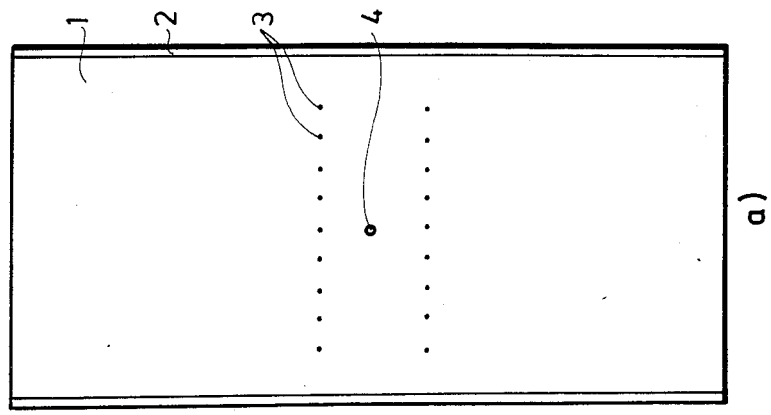

According to the invention when linear development is required to be achieved the OPLC chromatographic sheets sealed on the corresponding edges are superposed and thus put into the OPLC apparatus, so the sealed edges are placed over one another and the sides with the sorbent layer are set in the same direction. Thus though the cushion of the apparatus is streched onto the overtop layers only, but each chromatographic sheet serves as a cushion for the other sorbent layer being in connection with it. Thus each sorbent layer is under pressure and the eluent cannot penetrate into the sealed, practically impregnated or coated edges. However, this does not permit the efficient development of the chromatograms of the system consisting of several sorbent layers. The chromatographic sheets except the lower sheet (as shown in FIG. 1a) have to be holed in the same shape and size at the solvent inlet. This modification is made near the edge of the chromatographic sheet if linear, one-directional development is carried out (as shown in FIGS. 1b, 1c, 1d, 1e, 1f) while if the development is two-directional, the hole is in the middle of the chromatographic sheet (as shown in FIGS. 2a, 2b, 2c). The eluent can travel practically unhindered among the sorbent layers being on one another, thus the chromatograms can be developed simultaneously in the same manner.

The use of the sheets is similar to the use of the sheets for the techniques of TLC, HPTLC and OPLC. The edges of the sorbent layer (1) are sealed (2), the samples (3) are injected in front of the holed part (4, 6) of suitable shape and size. One can also use chromatographic sheets having a concentrating zone (7) comprising inactive sorbent.

Figure 3:
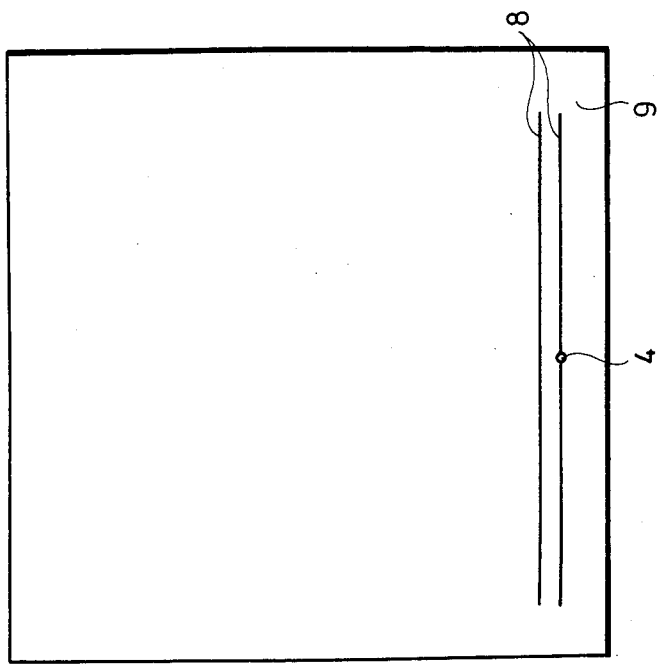
FIGS. 3(a) and (b) are, respectively, front and rear plan views of a chromatographic sheet having a channel formed at its back side for the overpressured chromatographic system of the invention.
Figure 3:
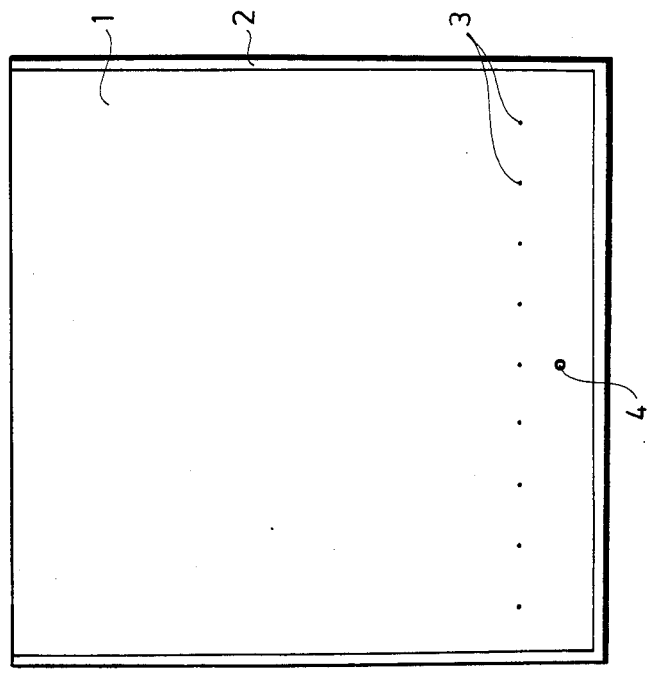

According to an embodiment of the invention (as shown in FIGS. 3a, 3b) a wedge or channel (8) is formed at the back side (9) of the chromatographic sheet.

The sheet or the system of that according to the invention can be shaped up from any elastic and/or less elastic and smooth (e.g. plastic, aluminium or glass) sheet with sorbent layer used in the over-pressured or conventional chromatographic techniques. The number of the sheets being able to be developed simultaneously has not any theoretical upper limit. According to the present stage of development of the overpressured technique 2 to 8 sheets can be developed simultaneously depending on the type of the apparatus. The size of the sheets and the direction of the migration of the eluent (one-directional, 2-directional, circular) can be chosen. Sheets with different kinds of sorbent layers can be developed simultaneously with the same eluent if their resistance is similar from the point of view of the migration of the eluent and they are geometrically congruent.

Figure 4:
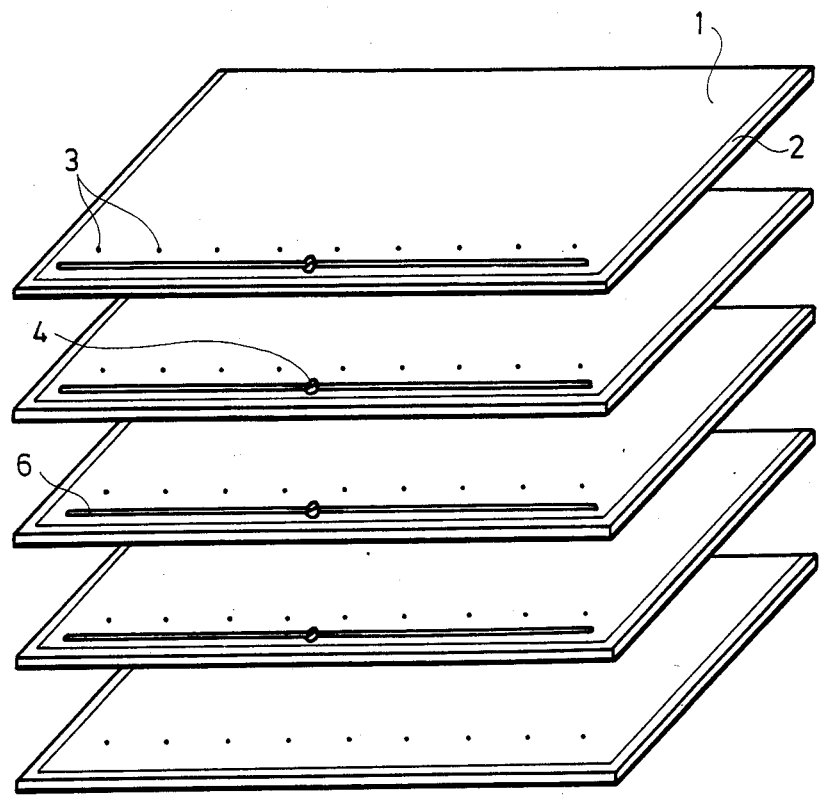
FIG. 4 is a perspective view of several chromatographic sheets in position to be superposed on one another in the overpressured chromatographic system of the invention.

Practically one can superpose the holed chromatographic sheets supplied with eluent leading channels on the sorbent-free side on one another in the apparatus. The upper layer can be covered by a closure chromatographic sheet supplied with leading channels, while a conventional, hole-free chromatographic sheet generally used in the overpressured layer-chromatographic techniques is applied as the lower layer (as shown in FIG. 4).

Figure 5:
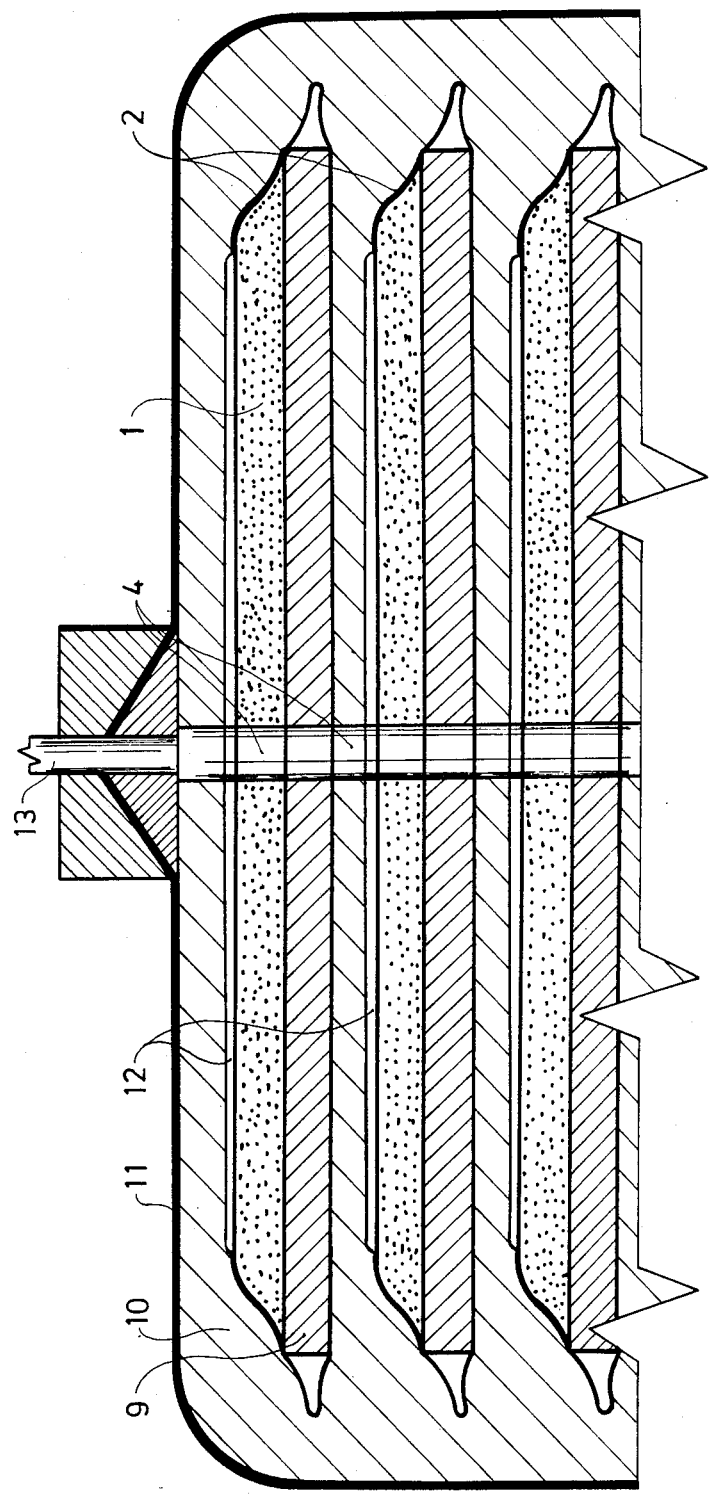
FIG. 5 is a cross section of an overpressured chromatographic system in accordance with the invention wherein the chromatographic sheets are in the form of a satchel.

One can couple an adequate number of holed covering sheets with leading channels in the form of a copybook or a satchel (as shown in FIG. 5), or each unit consisting of an adequate number of sheets and closure sheets can be thus joined to each other that they could be untied in a patent-like manner.

In order to fit the chromatographic sheets the gap blocks and the bottom sheet accurately to one another, leading mandrels can be formed on the upper gap block possessing with leading channel and hole. These mandrels the gap blocks can be strung to, the chromatographic sheets can be collided with and the mandrels can be joined to the holes formed for this purpose of the bottom sheet.

Figure 6:
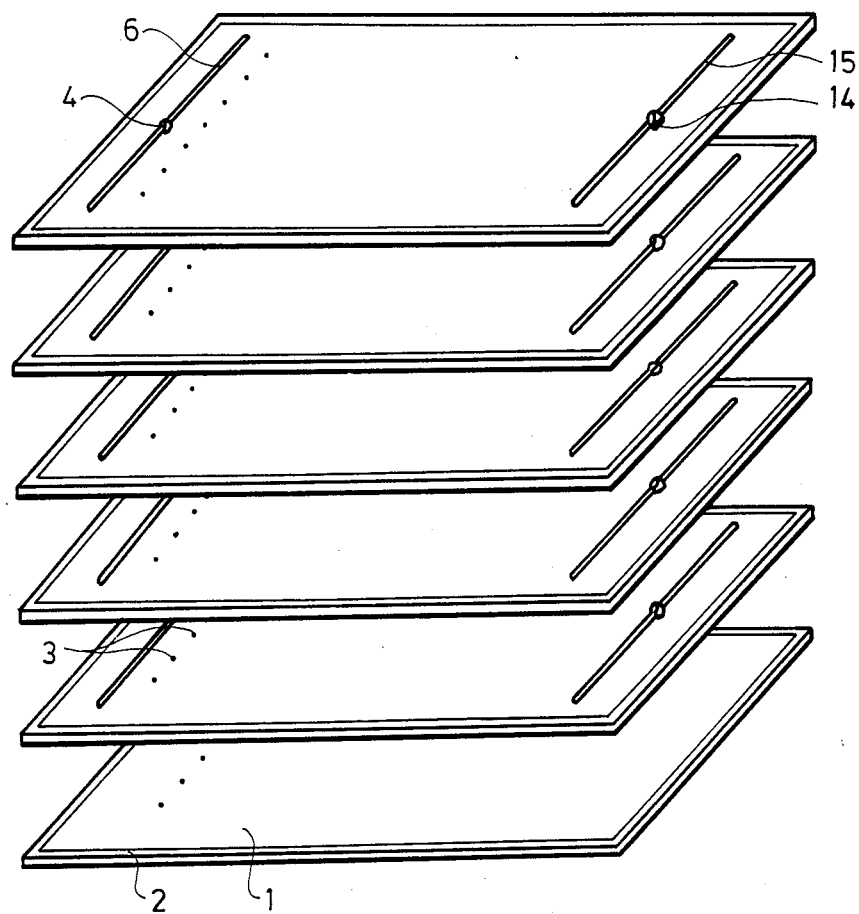
FIG. 6 is a perspective view of several chromatographic sheets in position to be superposed on one another in an embodiment of the overpressured chromatographic system of the invention wherein eluent is additionally led out from the chromatographic sheets.

The eluent can be led out from the chromatographic sheets sealed at all edges (as shown in FIG. 6) similarly to its leading in. On the opposite side of the eluent admission an other hole (14) is made and a mean-made known when the spreading of the eluent was described - is formed for the leading of the eluent. This mean collects and leads out the eluent in the end of the development. This solution gives a possibility for continuous development.

For the chromatographic sheet according to the invention inorganic (e.g. silica gel, aluminium oxide, talc) and organic (e.g. cellulose, polyamide) sorbents can be used. Siliceous earth glass and cellite can be employed as inactive sorbents.

When using the chromatographic sheets of the present invention more sheets of any size can be developed simultaneously, thus the capacity of the OPLC-apparatus increases significantly.

The technique using two or several chromatographic sheets simultaneously means a higher level of overpressured layer chromatography. The technique which can be entitled as overpressured multilayer chromatography is the most up-to-date variety of planar liquid chromatography and it can be effectively used in e.g. plant breeding, clinical laboratories and industrial control laboratories.

The invention is illustrated by the following, non-limiting examples.

EXAMPLE 1

Silica gel powder of 5 μm. average particle size is applied in a layer of 0.20 mm. thick onto a 20×20 cm. polyterephtalate sheet by the aid of polyacrylamide sticker of medium molar weight (dry substance content: 1.8%) thus, that 5—5 mm. stripes of the opposite edges remain uncovered. These parts are later covered with a water- and solvent-resistant polymer film. The chromatographic sheet is holed in the middle with a 160 mm. long, 2 mm. wide slit.

Onto four holed chromatographic sheets prepared by the same manner 15—15 samples of CAMAG II colour test material are applied in the same amount in a distance of 15—15 mm. from the hold slit and 10—10 mm. from each other. The spots of the samples are dried and the chromatographic sheets are precisely superposed on one another. The lower one is unholed but its edges are impregnated and samples also applied onto it. The system thus obtained is placed into an overpressured layer chromatographic apparatus and methylene chloride is used for the development.

The flow rate of the solvent is 185 cm$^3$/h., development time is 4.5 min. Under the given conditions the same front distance, $R_f$ value and diffusion are observed.

EXAMPLE 2

Silica gel powder of 5 μm. average particle size is applied in a layer of 0.25 mm. thick onto a 20×40 cm., 0.20 mm. thick aluminium sheet by the aid of polyvinyl acetate sticker (dry substance content: 2%) thus, that 5—5 mm. wide stripes on the opposite edges remain uncovered. These strips are later covered with a water- and solvent-resistant polymeric film. The chromatographic sheet is holed in the middle with a 182 mm. long, 0.8 mm. wide slit.

Onto two holed chromatographic sheets prepared by the same manner 15—15 samples containing 21 kinds of amino acids are applied in 1—1 μg. amino acid/spot amount in a distance of 15—15 mm. from the perforated slit and 10—10 mm. from each other. After the spots of the samples are dried, the chromatographic sheets are precisely superposed on one another. The lower sheet is not holed, but its edges are sealed and samples also applied onto it. The system thus obtained is placed onto an overpressured thin-layer chromatographic apparatus and a 4:1:1 mixture of n-butanol/glacial acetic acid/water is used as eluent. Development time: 65 min.

After development the disjointed chromatographic sheets are dried. One of the sheets is sprayed over with 0.2% ninhydrine reagent (0.2 g. of ninhydrine+80 cm$^3$. methanol+20 cm$^3$. acetic acid+0.05 g. of CuSO$_4$.5 H$_2$O) and heated at 100° C. for 5 minutes. The coloured chromatogram thus obtained is evaluated with spectrophotometer. ±1.5% difference by amino acids were observed in the case of the 2×15 samples.

The other dried chromatographic sheet is sprayed over with Sakaguchi reagent. Thus arginine can be specifically detected and its quantity can be determined. The third chromatographic sheet is sprayed over with o-phthaldialdehyde reagent and the chromatogram thus obtained is evaluated in UV light by chromatogram spectrophotometer.

EXAMPLE 3

The process of Example 1 was followed except four chromatographic sheet with different sorbent layers are applied. The sorbent layer of the lower chromatographic sheet is silica gel of 5 μm. average particle size; the seconds is inert aluminium oxide of 5 μm. average particle size; the thirds magnesium silicate of 5 μm. average particle size; while the fourths is siliceous earth of 5 μm. average particle size. Under the given conditions not significantly different front-distances, $R_f$ values characteristic for the sorbents and spot diameters were observed.

EXAMPLE 4

Silica gel powder of 3 μm. average particle size is applied in a layer of 0.15 mm. stick onto a 20×20 cm. polyterephtalate sheet by the aid of polyacryloamide sticker of high molar weight (dry substance content: 1.7%) thus, that three edges of the chromatographic sheet is impregnated with a polymeric dispersion. The chromatographic sheet thus obtained is holed with a 185 mm. long, 1 mm. wide slit close to the uneven sealed edge.

Onto five holed chromatographic sheets prepared by the same manner 5×15 samples of petrolether extract of wild chamomille flowers are applied in aliquote amount in a distance of 15 mm. from the perforated slit and 10—10 mm. from each other. After the spots of the sample application are dried, the chromatographic sheets are precisely superposed on one another. The lower chromatographic sheet is not holed but its edges are impregnated and samples also applied onto it. The system thus obtained is placed into an overpressured layer chromatographic apparatus and benzene is used as eluent. Development time: 15.5 min.

After development the disconnected chromatographic sheets are dried, thereafter sprayed over with conc. sulphuric acid containing 0.2% of vanilline. The chromatograms are evaluated visually and by chromatogram spectrophotometer. The data concerning the essential oils comprised by wild chamomille are used for chemotaxonomical and breeding tests.

EXAMPLE 5

The procedure of Example 4 is followed, but such a chromatographic sheet is used wherein a concentrating zone is formed. The inactive stripe is silicious earth while the active stripe comprises silica gel of 3 μm. average particle size. Due to the concentrating effect the essential oil components of wild chamomille can be observed in sharply defined stripes, the resolving power is better, than in Example 4.

EXAMPLE 6

The procedure of Example 4 is followed, but 2—2 eluent leading channels are formed, on the adsorbent-free side of the chromatographic sheets. A gap block with eluent-leading channels is used for the leading of the solvent on the upper sorbent layer. The lower chromatographic sheet is an unholed, conventional overpressed chromatographic sheet.

EXAMPLE 7

The procedure of Example 4 is followed, but each sorbent layer is covered by a holed cover sheet supplied with leading channels.

EXAMPLE 8

Silica gel powder of 5 μm. average particle size is applied in a layer of 0.20 mm. thick onto a 10×20 cm. aluminium foil by the aid of poliacryloamide sticker of medium molar weight (dry substance content: 1.5%). Three of the edges of the foil is impregnated with a polymeric dispersion in 3 mm. width. The chromatographic sheet is holed close to the uneven sealed edge by a 80 mm. long, 0.5 mm. wide slit. 15—15 samples of 1 μl. amount are applied onto the chromatographic sheet in a distance of 15 mm. from the holed slit. The samples comprise formaldimedone obtained from human urine precipitated by dimedone. (The compounds of 25 ml. of urine are dissolved in 1 $cm^3$. of chloroform.) Four of the chromatographic sheets are put into a bag formed from 5 pieces of perforated cover sheets supplied with leading channels and this system is used in overpressured layer chromatographic apparatuses.

A 95:5 mixture of benzene/ethyl acetate is used as eluent (developing time: 12 min., external cushion pressure: 1.2 MPa). The reagent is 0.2% 2,6-dichlorokinone-chlorokinone-chloroimide in methanolic solution, and after drying 10% aqueous sodium carbonate solution. The chromatograms were evaluated visually, regarding the quantities of the compounds. The data thus obtained can be used in diagnostic tests.

EXAMPLE 9

The procedure of Example 8 is followed, but such cover sheets are used which are supplied with holed channels not only for the admission but the leading out of the solvent. Thus the eluent can be overmigrated which results in a better resolution.

We claim:

1. An overpressured multilayer chromatographic system comprising at least two chromatographic sheets superposed relative to one another, each of said chromatographic sheets including a sorbent layer on one side, said respective sorbent layers being sealed at at least one of their respective edges, at least one of said chromatographic sheets having a hole formed therethrough of adequate size and shape for eluent inlet and an eluent leading channel formed proximate to said hole to provide a linear eluent front, and the lowermost of the superposed chromatographic sheets being without a hole.

2. The overpressured multi-layer chromatographic system of claim 1 wherein at least one of said sorbent layers is sealed by coating with a polymer film.

3. The overpressured multi-layer chromatographic system of claim 1 wherein said sorbent layer is sealed by impregnation.

4. The overpressured multi-layer chromatographic system of claim 1 wherein three edges of the chromatographic sheets are sealed and said hole in at least one of said chromatographic sheets is proximate to the uneven sealed edge.

5. The overpressured multi-layer chromatographic system of claim 1 wherein at least one of said chromatographic sheets is sealed at its opposite edges and the hole is in the middle of the at least one said sheet.

6. The overpressured multi-layer chromatographic system of claim 1 wherein at least one of said sheets further includes a second hole, said second hole being of adequate size and shape for leading of the eluent out of the sheet.

7. The chromatographic system of claim 6 wherein said second hole is on the opposite end of the sheet to that having the first hole.

8. The chromatographic system of claim 1 wherein at least one chromatographic sheet includes an inert sorbent concentration zone proximate to the hole.

9. The chromatographic system of claim 1 wherein said eluent leading channel is formed on the sorbent free side of said at least one said chromatographic sheet.

10. The chromatographic system of claim 1 wherein the hole comprises an eluent leading slit at right angles to the direction of development.

11. The chromatographic system of claim 1 wherein said lowermost chromatographic sheet comprises a conventional chromatographic sheet without a hole.

12. The chromatographic system of claim 1 wherein the chromatographic sheets include one side coated with a sorbent and one side not sorbent coated and are superposed upon each other such that the nonsorbent coated sides of at least one said superposed chromatographic sheet serves as a cover sheet for the sorbent of another sheet.

13. The chromatographic system of claim 12 further comprising a conventional chromatographic sheet not including a hole serving as the bottom layer.

* * * * *